(12) United States Patent
Canizares, Jr. et al.

(10) Patent No.: US 8,459,155 B2
(45) Date of Patent: Jun. 11, 2013

(54) MODIFIED FASTENER AND INSERTION TOOL

(75) Inventors: Eduardo Antonio Canizares, Jr., Worcester, MA (US); Graham Smith, Newburyport, MA (US)

(73) Assignee: Smith & Nephew, Inc., Andover, MA (US)

( * ) Notice: Subject to any disclaimer, the term of this patent is extended or adjusted under 35 U.S.C. 154(b) by 257 days.

(21) Appl. No.: 12/875,244

(22) Filed: Sep. 3, 2010

(65) Prior Publication Data
US 2012/0057949 A1    Mar. 8, 2012

(51) Int. Cl.
   *B25B 23/08*    (2006.01)
   *F16B 23/00*    (2006.01)

(52) U.S. Cl.
   USPC .............................. 81/451; 411/410; 411/407

(58) Field of Classification Search
   USPC ............ 81/451, 461, 176.2; 29/428; 411/402, 411/403, 405, 407, 410; 606/305, 308
   See application file for complete search history.

(56) References Cited

U.S. PATENT DOCUMENTS

| | | | | |
|---|---|---|---|---|
| 2,566,055 A | * | 8/1951 | Daderko, Sr. et al. | 81/436 |
| 3,302,672 A | * | 2/1967 | Walton | 81/461 |
| 3,424,212 A | * | 1/1969 | Kemper | 81/436 |
| 4,936,172 A | * | 6/1990 | Jackson | 81/451 |
| 5,214,987 A | * | 6/1993 | Fenton, Sr. | 81/460 |
| 5,269,208 A | * | 12/1993 | Kolvites et al. | 81/176.2 |
| 5,353,667 A | * | 10/1994 | Wilner | 81/436 |
| 5,358,368 A | * | 10/1994 | Conlan et al. | 411/410 |
| 5,438,895 A | * | 8/1995 | Bassell et al. | 81/451 |
| 5,590,574 A | | 1/1997 | Lide | |
| 5,791,212 A | | 8/1998 | Han | |
| 5,913,650 A | * | 6/1999 | Daoud | 411/410 |
| 6,089,396 A | * | 7/2000 | Pozek | 220/251 |
| 6,148,699 A | * | 11/2000 | Han | 81/451 |

(Continued)

FOREIGN PATENT DOCUMENTS

| CN | 201 351 663 Y | 11/2009 |
|---|---|---|
| CN | 201351663 T | 11/2009 |

(Continued)

OTHER PUBLICATIONS

International Search Report and Written Opinion for PCT/US2011/049251 mailed Nov. 25, 2011.

(Continued)

*Primary Examiner* — David B Thomas
(74) *Attorney, Agent, or Firm* — Pierce Atwood LLP; Joseph M. Maraia

(57) ABSTRACT

According to example configurations, a modified screw head includes one or more slots or grooved channels. A screwdriver device includes a tip that can be inserted into a cavity in the head of the screw to torque the modified screw into an object. The screwdriver device includes a sleeve. The sleeve slides along a shaft of the screwdriver. The sleeve includes inward protruding posts (e.g., pins, fingers, etc.). Sliding of the sleeve over the screw's head requires that inward protruding posts in the sleeve be aligned with the grooves on the sidewall of the screw's head. Subsequent to aligning and sliding the sleeve into the grooved channels of the screw's head, the user twists the sleeve to secure the screw head to the screwdriver's tip. The sleeve can be spring-loaded to pull the head of the screw toward a handle end of the screwdriver after a user releases the sleeve.

48 Claims, 17 Drawing Sheets

U.S. PATENT DOCUMENTS

| | | | |
|---|---|---|---|
| 6,149,653 A * | 11/2000 | Deslauriers | 606/232 |
| 6,244,141 B1 | 6/2001 | Han | |
| 6,293,745 B1 * | 9/2001 | Lu | 411/410 |
| 6,334,748 B1 | 1/2002 | Gudjonsson | |
| 6,402,757 B1 | 6/2002 | Moore, III et al. | |
| 6,481,944 B2 * | 11/2002 | Mann et al. | 411/403 |
| 6,543,317 B1 | 4/2003 | Rinner et al. | |
| 6,672,404 B2 | 1/2004 | Kamo et al. | |
| 6,755,836 B1 * | 6/2004 | Lewis | 606/916 |
| 6,857,343 B1 | 2/2005 | Easterbrooks et al. | |
| 7,073,416 B2 * | 7/2006 | Kozak et al. | 81/460 |
| 7,174,615 B2 | 2/2007 | Mark et al. | |
| 7,261,716 B2 * | 8/2007 | Strobel et al. | 606/314 |
| 7,406,899 B2 * | 8/2008 | Walker | 81/434 |
| 7,448,300 B2 * | 11/2008 | Barniak, Jr. | 81/124.2 |
| 7,452,361 B2 | 11/2008 | Kreidler | |
| 7,461,574 B2 * | 12/2008 | Lewis et al. | 81/57.37 |
| 7,475,618 B1 | 1/2009 | Pardue et al. | |
| 7,494,311 B2 * | 2/2009 | Fuerle | 411/407 |
| 7,581,909 B2 * | 9/2009 | Szoke | 411/401 |
| 7,652,886 B2 * | 1/2010 | Li et al. | 361/719 |
| 7,713,013 B2 * | 5/2010 | Sedgwick et al. | 411/411 |
| 7,883,529 B2 * | 2/2011 | Sinnott et al. | 606/232 |
| 7,955,364 B2 * | 6/2011 | Ziolo et al. | 606/308 |
| 8,002,811 B2 * | 8/2011 | Corradi et al. | 606/300 |
| 2004/0093032 A1 * | 5/2004 | Sinnott et al. | 606/232 |
| 2007/0005070 A1 | 1/2007 | Kay et al. | |
| 2007/0212190 A1 | 9/2007 | Monday et al. | |
| 2008/0288002 A1 * | 11/2008 | Crall et al. | 606/308 |
| 2009/0042164 A1 | 2/2009 | Machata et al. | |
| 2010/0111641 A1 * | 5/2010 | Zoller | 411/403 |

FOREIGN PATENT DOCUMENTS

| | | |
|---|---|---|
| DE | 296 21 364 U1 | 2/1997 |
| DE | 29621364 U1 | 2/1997 |
| EP | 1561 429 A1 | 8/2005 |
| EP | 1561429 A1 | 8/2005 |
| GB | 225 620 A | 12/1924 |
| GB | 225620 A | 12/1924 |
| GB | 840 369 A | 7/1960 |
| GB | 840369 A | 7/1960 |
| WO | WO 99 11177 A2 | 3/1999 |
| WO | WO99/11177 A2 | 3/1999 |

OTHER PUBLICATIONS

Search Report dated Nov. 25, 2011, PCT/US2011/049251, pp. 2.

* cited by examiner

MODIFIED FASTENER AND INSERTION TOOL

BACKGROUND

Conventional screw driving devices provide different ways of holding a screw in position while the screw is driven into a work material such as a wall, wood, bone, etc.

For example, one type of conventional screwdriver includes a magnetized driving bit to hold a respective metal screw to the bit during installation. Even if the magnetic driving bit can initially hold the screw perpendicularly with respect to a work material, the driving bit may have poor holding power. As a result, the screw can easily tilt to an undesirable angle when uneven force is applied on the head of the screw. Moreover, when non-ferrous screws are used, the magnetized driving bit does not serve any useful purpose as the operator must manually hold the screw in place.

Another type of conventional screwdriver includes an assembly whose mouth widens to accept and hold a screw. For example, a conventional screwdriver in U.S. Patent Publication 2009/0042164 includes an orthodontic driver tip that is configured for screwing and unscrewing an orthodontic bone screw. This conventional driver tip includes an elongated inner rod having an enlarged diameter front tip portion that widens to accept a screw head. The tip portion comprises multiple extending resilient arms, which define an opening recess. The resilient arms are pushed apart to increase a diameter of the opening and accept a screw head. A sleeve is mounted on the rod of varying diameter. A locking mechanism releasably secures the arms against lengthwise movement along the rod when the locking mechanism is moved forward to a position wherein the arms are bent into engagement with the head of a bone screw disposed inside the front tip portion.

This latter described type of conventional screwdriver also suffers from a number of drawbacks. For example, during use, a user may apply an excessive amount of force to a screwdriver to insert the screw into an object. If the screwdriver does not properly hold the screw to the tip of the screwdriver during the insertion because the assembly at the tip secures the screw using only a weak force, the screw can disengage from the driver bit assembly and potentially harm the user and/or the object into which the screw is being driven. Also, it is undesirable in certain applications such as surgery that the opening of a screw holder assembly at the tip of a conventional screwdriver must be widened to a larger diameter to release a screw head from a driving bit.

BRIEF DESCRIPTION

Embodiments herein include a novel fastener and corresponding insertion tool to drive the fastener into an object.

For example, in accordance with one embodiment herein, a fastener includes threads and a head. The threads are disposed at a first axial end of the fastener. The head is disposed at a second axial end of the fastener opposite the threads. The head of the fastener includes a cavity in which to receive a driving bit disposed at an end of an insertion tool. The head of the fastener also includes one or more grooved channels or cavities in which to secure the head of the fastener to the driving bit. For example, a post can occupy each of the grooved channels to secure the head to the fastener.

In accordance with more specific embodiments, the one or more grooved channels in the screw can be cavities disposed on an outer sidewall surface of the head. Accordingly, a first cavity in the head of the fastener can be used to apply torque to the fastener and screw the fastener into an object. The one or more cavities on the sidewall of the fastener's head can be used to hold the head of the fastener on to the driving bit.

Each grooved channel or cavity disposed on the sidewall surface of the fastener's head can be a substantially J-shaped grooved channel or T-shaped grooved channel to receive a post of the insertion tool. One or more posts can be affixed to a sleeve of the insertion tool to secure the head of the fastener to a driving bit disposed at the end of the insertion tool.

A core along an axial length of the fastener can be hollow. Providing a hollowed center in the fastener is useful for applications in which the fastener is a bone screw inserted into a bone.

In the case of more than one grooved channel on the outer sidewall of the fastener head, the channels can be circumferentially spaced apart from each other. Via occupation of a post or other suitable protrusion into each of the grooved channels, the insertion tool can apply a force on the head of the fastener to secure the fastener to a driving tip of the insertion tool.

In one embodiment, each of the grooved channels on the head of the fastener is configured to receive a post disposed on the inside of a sliding sleeve of the insertion tool. A force can be applied to the sleeve (and thus corresponding posts affixed to the sleeve) to hold the head of the fastener to the driving bit of the insertion tool.

Each of the grooved channels can include an opening and a termination. The opened end of a grooved channel receives a post or protrusion associated with the insertion tool. The termination end of a grooved channel prevents the sleeve from sliding further when the post of the sleeve contacts the termination in the respective grooved channel. In accordance with one embodiment, the opening of a grooved channel can receive a post moved in a direction toward the threads on the fastener; a termination end of the grooved channel prevents sliding of the post in a direction away from the threads of the fastener.

Embodiments herein further include an insertion tool for inserting a fastener into work material. The insertion tool includes a shaft, a handle disposed at a first axial end of the shaft, and a driving bit disposed at a second axial end of the shaft. The driving bit can be configured to occupy a cavity disposed in a head of a fastener. The insertion tool can further include at least one post (e.g., pin, finger, protrusion, etc.) to occupy at least one respective grooved channels disposed on the head of the fastener to hold the fastener to the driving bit. The post of the insertion tool is movable in a radial and/or linear manner. In one embodiment, the at least one post can be moved or inserted into the at least one respective grooved channels of the screw head.

In certain embodiments, the driving bit is fixedly attached to the shaft; the shaft is fixedly attached to the handle of the insertion tool. The posts are fixed to a sleeve that slides along the shaft of the insertion tool.

The sleeve of the insertion tool can be spring-loaded to pull the head of the fastener towards a handle of the insertion tool opposite threads on the fastener.

A diameter of the sleeve nearer the first axial end of the shaft can be greater than a diameter of the sleeve nearer the second axial end of the shaft. Accordingly, a user operating the insertion tool can easily apply a force on the sleeve to overcome the spring and engage the posts into the grooved channels of the fastener.

The sleeve of the insertion tool can rotate around the shaft. Rotating the sleeve can facilitate engaging of the posts in the sleeve into the grooved channels. In one embodiment, the posts are affixed to the sleeve as discussed above. Movement (e.g., sliding and rotating) of the sleeve causes the posts to move along an axis parallel to the shaft and rotate about the shaft to secure the head of the fastener to the driving bit.

While in a resting position, such as when no force is applied to the spring-loaded sleeve, the sleeve of the insertion tool can reside in a resting position in which the driving tip of the insertion tool is exposed for access. In such a position, the user can insert the driving tip of the insertion tool into a cavity in the head of a fastener. Accordingly, the sleeve can be configured to slide along the shaft of the insertion tool to expose the driving bit for insertion of the driving bit into a cavity in the head of the fastener.

The shaft of the insertion tool can be hollow. As previously discussed, the fastener also can be hollow. Accordingly, a string or guide-wire can be pulled through a combination of the shaft and the fastener to facilitate insertion of the fastener during surgery.

Embodiments herein further include a method of creating a novel fastener as discussed herein. For example, a machine receives a fastener. The fastener includes a head disposed at a first axial end of the fastener and threads disposed at a second axial end of the fastener. The head of the fastener may include a cavity in which to receive a driving bit of an insertion tool. The machine then produces at least one grooved channel on a surface of the head of the fastener. Producing the grooved channel can include removing a portion of material in the head to produce multiple spaced grooved channels on an outer, circumferential surface of the head. In accordance with other embodiments, the screw can be cast in a mold to include one or more grooved channels.

Embodiments herein further include use of a screwdriver tool and novel fastener as discussed herein. For example, a user receives a fastener. The user inserts a driving bit of a screwdriver tool into a cavity at an end of the fastener. The user then initiates insertion of posts of the screwdriver tool into grooved channels disposed on sidewalls of the fastener to secure the fastener to the driving bit.

The insertion tool can include a sleeve that slides along a shaft of the screwdriver. The posts can be fixedly attached to the sleeve. Insertion of the posts into the grooved channels can be achieved by sliding the sleeve along a shaft of the screwdriver tool towards the fastener to insert or slide the posts in to the grooved channels. In addition to sliding the sleeve, a user can rotate the sleeve about the shaft of the screwdriver tool to secure or lock the posts into the grooved channels of the fastener. In accordance with such an embodiment, the posts in the sleeve pull on the head of the screw to secure the fastener to the driving tip of the insertion tool.

As previously discussed, the sleeve can be spring-loaded. Subsequent to sliding and rotating the sleeve, the user can release the spring-loaded sleeve to enable the spring-loaded sleeve to automatically pull the head of the fastener towards a handle end of the screwdriver tool. In other words, the sleeve of the screwdriver tool can be configured to pull the head of the fastener onto the driving bit when engaged in the grooved channels of the fastener.

For example, in accordance with one embodiment herein, a fastener includes threads and a head. The threads are disposed at a first axial end of the fastener. The head is disposed at a second axial end of the fastener opposite the threads. The head of the fastener includes a cavity in which to receive a driving bit disposed at an end of an insertion tool. The head of the fastener also includes one or more posts in which to secure the head of the fastener to the driving bit. For example, a post of the fastener can occupy each of the channels of the insertion tool to secure the head to the fastener.

The one or more posts on the sidewall of the fastener's head can be used to hold the head of the fastener on to the driving bit.

Each post disposed on the sidewall surface of the fastener's head can be received by a substantially J-shaped or substantially T-shaped channel of the insertion tool.

A core along an axial length of the fastener can be hollow. Providing a hollowed center in the fastener having multiple posts is useful for applications in which the fastener is a bone screw inserted into a bone.

In the case of more than one post on the outer sidewall of the fastener head, the posts can be circumferentially spaced apart from each other. Via occupation of a post or other suitable protrusion in the fastener into each of the grooved channels of the insertion tool, the insertion tool can apply a force on the head of the fastener to secure the fastener to a driving tip of the insertion tool.

In one embodiment, each of the posts on the head of the fastener is configured to be received by a channel disposed on a sliding sleeve of the insertion tool. A force can be applied to the sleeve (and thus corresponding channels of the sleeve) to hold the head of the fastener to the driving bit of the insertion tool.

Each of the channels on the sleeve of the insertion tool can include an opening and a termination. The opened end of a grooved channel receives a post or protrusion associated with the fastener. The termination of the channel in the sleeve locks the head of the fastener to the driving bit of the insertion tool.

Embodiments herein further include an insertion tool for inserting a fastener having multiple posts into work material. The insertion tool includes a shaft, a handle disposed at a first axial end of the shaft, and a driving bit disposed at a second axial end of the shaft. The driving bit can be configured to occupy a cavity disposed in a head of a fastener. The insertion tool can further include at least one channel for receiving at least one respective post disposed on the head of the fastener to hold the fastener to the driving bit. The channel of the insertion tool is movable in a radial and/or linear manner. In one embodiment, the at least channel can be moved to receive respective at least one post on the head of the fastener.

In certain embodiments, the driving bit is fixedly attached to the shaft; the shaft is fixedly attached to the handle of the insertion tool. The channels are produced in a sleeve that slides along the shaft of the insertion tool.

The sleeve of the insertion tool can be spring-loaded to pull the head of the fastener towards a handle of the insertion tool opposite threads on the fastener.

The sleeve of the insertion tool can rotate around the shaft. Rotating the sleeve can facilitate engaging of the channels in the sleeve to the posts in the fastener. In one embodiment, the channels are disposed in the sleeve as discussed above. Movement (e.g., sliding and rotating) of the sleeve with respect to an axis parallel to the shaft enables engagement of the posts of the fastener into the channels of the sleeve to secure the head of the fastener to the driving bit.

While in a resting position, such as when no force is applied to the spring-loaded sleeve, the sleeve of the insertion tool can reside in a resting position in which the driving tip of the insertion tool is exposed for access. In such a position, the user can insert the driving tip of the insertion tool into a cavity in the head of a fastener. Accordingly, the sleeve can be configured to slide along the shaft of the insertion tool to expose the driving bit for insertion of the driving bit into a cavity in the head of the fastener.

The shaft of the insertion tool can be hollow. As previously discussed, the fastener having multiple posts also can be hollow. Accordingly, a string or guide-wire can be pulled through a combination of the shaft and the fastener to facilitate insertion of the fastener during surgery.

Embodiments herein further include a method of creating a novel fastener as discussed herein. For example, a machine receives a fastener. The fastener includes a head disposed at a first axial end of the fastener and threads disposed at a second axial end of the fastener. The head of the fastener may include a cavity in which to receive a driving bit of an insertion tool. The machine then produces at least one post on a surface of the head of the fastener. Producing the posts can include removing a portion of material in the head to and inserting a respective pin. In accordance with other embodiments, the screw can be cast in a mold to include one or more posts extending axially outward from the head.

Embodiments herein further include use of a screwdriver tool and novel fastener as discussed herein. For example, a user receives a fastener. The user inserts a driving bit of a screwdriver tool into a cavity at an end of the fastener. The user then initiates engagement of posts in the fastener into channels disposed on a sleeve of the insertion tool to secure the fastener to the driving bit.

As previously discussed, the insertion tool can include a sleeve that slides along a shaft of the screwdriver. The channels can be formed in the sleeve to receive the posts of the fastener. Receipt of the posts of the fastener into the channels of the sleeve can be achieved by sliding the sleeve along the shaft of the screwdriver tool towards the fastener to engage the posts into the channels. In addition to sliding the sleeve, a user can rotate the sleeve about the shaft of the screwdriver tool to secure or lock the posts of the fastener into the channels of the sleeve. In accordance with such an embodiment, the channels in the sleeve pull on the head of the screw to secure the fastener to the driving tip of the insertion tool.

As previously discussed, the sleeve can be spring-loaded. Subsequent to sliding and rotating the sleeve, the user can release the spring-loaded sleeve to enable the spring-loaded sleeve to automatically pull the head of the fastener towards a handle end of the screwdriver tool. In other words, the sleeve of the screwdriver tool can be configured to pull the head of the fastener onto the driving bit when the posts of the fats are engaged in the channels in the sleeve of the insertion tool.

These and other example embodiments are discussed in more detail below.

As discussed above, techniques herein are well suited for use in securing a fastener to a tip of a driving device. However, it should be noted that embodiments herein are not limited to use in such applications and that the techniques discussed herein are well suited for other applications as well.

Note that although each of the different features, techniques, configurations, etc., herein may be discussed in different places of this disclosure, it is intended that each of the concepts can be utilized independently of each other or, where suitable, in combination with each other. Accordingly, the one or more present inventions as described herein can be embodied and viewed in many different ways.

Also, note that this preliminary discussion of embodiments herein does not specify every embodiment and/or incrementally novel aspect of the present disclosure or claimed invention(s). Instead, this brief description only presents general embodiments and corresponding points of novelty over conventional techniques. For additional details and/or possible perspectives (permutations) of the invention(s), and additional points of novelty, the reader is directed to the Detailed Description section and corresponding figures of the present disclosure as further discussed below.

BRIEF DESCRIPTION OF THE DRAWINGS

The foregoing and other objects, features, and advantages of the invention will be apparent from the following more particular description of preferred embodiments herein, as illustrated in the accompanying drawings in which like reference characters refer to the same parts throughout the different views. The drawings are not necessarily to scale, with emphasis instead being placed upon illustrating the embodiments, principles, concepts, etc.

DETAILED DESCRIPTION

In accordance with one embodiment, a modified screw includes one or more, grooved channels on an outer surface or sidewall of the screw's head. A screwdriver device includes a tip that can be inserted into a cavity at the head of the screw to torque the modified screw. In one embodiment, the screwdriver includes a movable assembly such as a sleeve. The sleeve includes posts (e.g., protrusions, pins, fingers, etc.) protruding inward. Sliding of the sleeve along a shaft of the screwdriver device over the screw head requires that inward protruding posts in the sleeve be rotated and aligned with the grooves on the sidewall of the screw's head. Subsequent to aligning and sliding the sleeve along the shaft to engage the posts in the grooved channels, the user twists the sleeve to lock the posts in the grooved channels and secure the fastener's head to the tip of the screwdriver. To hold a fastener to the insertion tool, the sleeve can be spring-loaded to automatically pull the head of the screw toward a handle end of the screwdriver after a user releases the sleeve.

Figure 1:
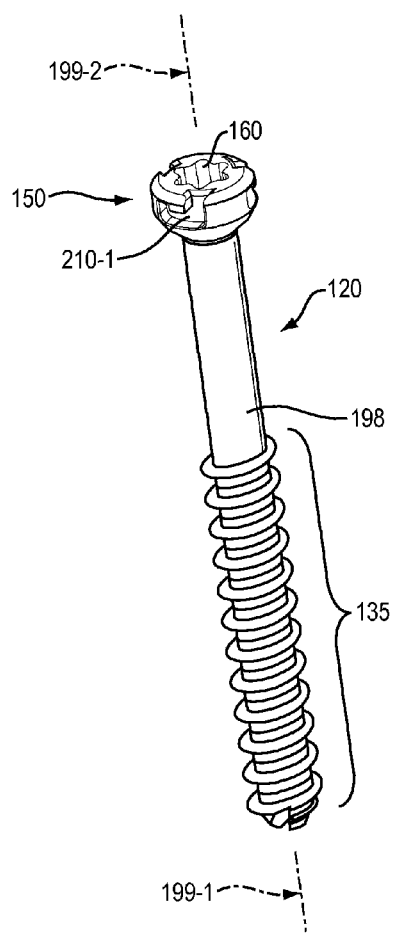
FIG. 1 is an example perspective view of a fastener according to embodiments herein.

More specifically, FIG. 1 is an example perspective view of a fastener according to embodiments herein.

In accordance with one embodiment herein, fastener 120 includes threads 135 and a head 150. The threads 135 are disposed at a first axial end 199-1 of axis 198 of the fastener 120. The head 150 is disposed at a second axial end 199-2 of axis 198 of the fastener 120. The head 150 of the fastener 120 includes a cavity 160 in which to receive a driving bit disposed at an end of an insertion tool such as a screwdriver. The head of the fastener 120 also includes grooved channel 210-1.

By way of a non-limiting example, the cavity 160 in fastener 120 is configured to receive a torx bit disposed at the end of an insertion tool. However, note that the cavity 160 of head 150 can be bored to receive any suitable type of driving bit (e.g., a phillips head bit, flat head bit, hex bit, socket, etc.).

Also, note that the image of fastener 120 including threads 135 is shown by way of non-limiting example only. The fastener 120 according to further embodiments herein can be configured to have different types of holding features, other than merely threads 135, such as barbs, hooks, or other suitable shaped features on axial end 199-1 of the fastener 120 that would allow for increased fixation of the fastener 120 to tissue. In the instance where the fastener 120 includes barbs, hooks, etc., a respective insertion tool as discussed below can be used to axially drive the fastener 120 into an object as opposed to rotationally driving threads 135 of the fastener 120 into work material such as a tissue.

Figure 2A:
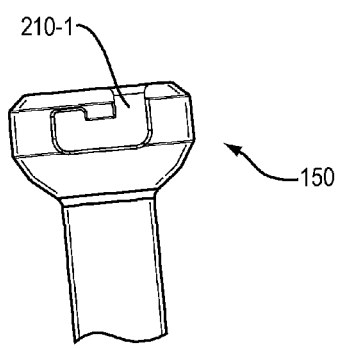
FIG. 2A is an example side view of a fastener according to embodiments herein.

FIG. 2A is an example side view of a fastener according to embodiments herein. As shown, the head of the fastener 120 includes grooved channel 210-1 as discussed above. As will be discussed later in this specification, the grooved channel 210-1 facilitates securing the head 150 of the fastener 120 to a corresponding driving bit of an insertion tool.

Figure 2B:
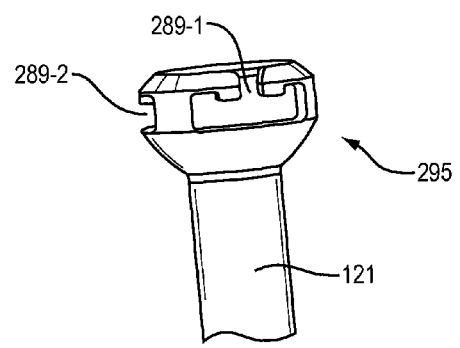
FIG. 2B is an example side view of a fastener according to embodiments herein.

In accordance with more specific embodiments as shown, the grooved channel 210-1 can be disposed on an outer sidewall surface of the head 150 of fastener 120. A machine can be used to remove material from the head 150 of fastener to create the grooved channel 210-1 (i.e., cavity). The fastener also can be manufactured via a mold or a combination of a mold and execution of machine to remove material from the head 150. Other suitable methods of manufacturing the fastener 120 may also be used. FIG. 2B is an example side view of a fastener according to embodiments herein. As shown, the example head 295 of the fastener 121 includes T-shaped grooved channels 289 (e.g., grooved channel 289-1, grooved channel 289-2, . . . ). The grooved channels 289 in fastener 121 facilitate securing the head 295 of the fastener 120 to a corresponding driving bit of an insertion tool.

In accordance with more specific embodiments as shown, the grooved channel 289-1 can be disposed on an outer sidewall surface of the head 295 of fastener 121. A machine can be used to remove material from the head 295 of fastener 121 to create the grooved channels 289. Note that the fastener 121 also can be manufactured via a mold or a combination of a mold and execution of machine to remove material from the head 295. Other suitable methods of manufacturing the fastener 121 may also be used.

Use of fastener 121 is similar to use of fastener 120 except that fastener 121 enables a user to rotate a respective sleeve of an insertion tool either clockwise or counter-clockwise to engage posts on the sleeve into the grooved channels 289.

Figure 3:
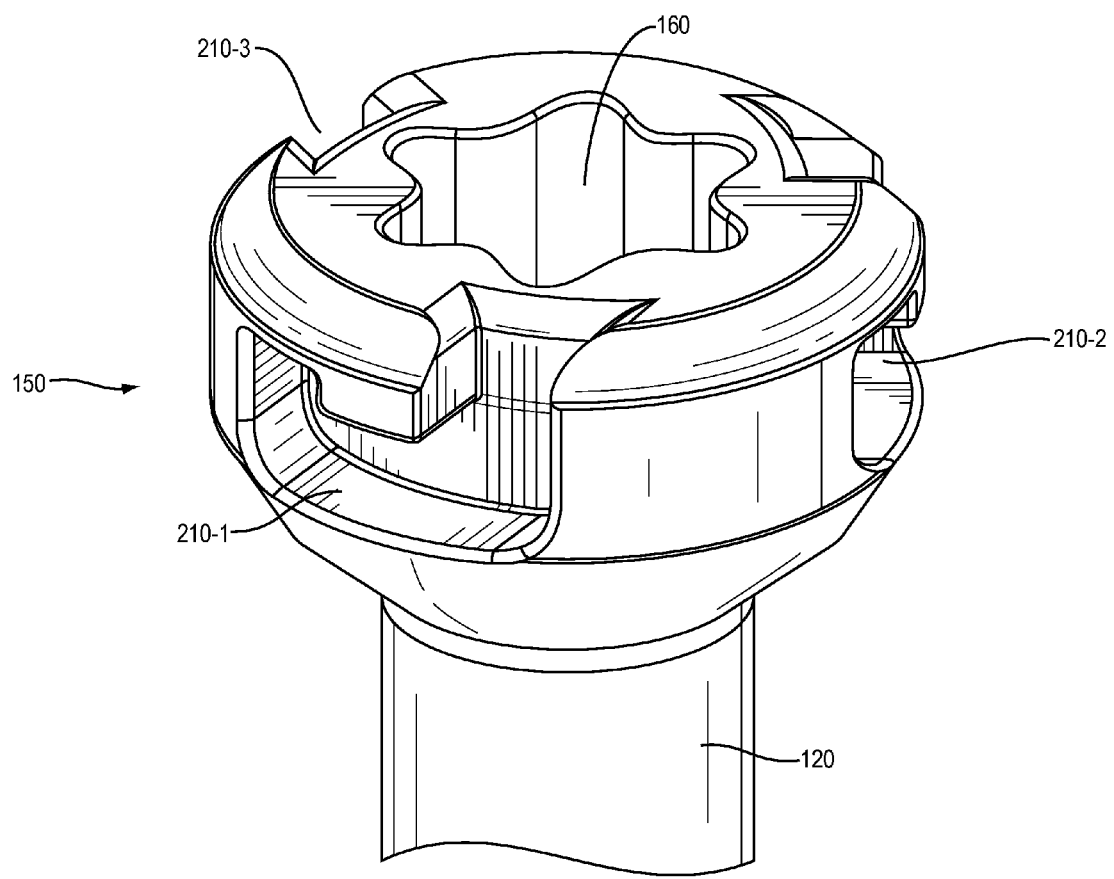
FIG. 3 is an example perspective view of the head of a fastener according to embodiments herein.

FIG. 3 is an example perspective view of a fastener according to embodiments herein.

As shown, fastener 120 in FIG. 3 includes multiple grooved channels 210 (e.g., grooved channel 210-1, grooved channel 210-2, and grooved channel 210-3). Although head 150 includes three grooved channels 210 as shown in FIG. 3, head 150 can be configured to include any suitable number of grooved channels 210 disposed thereon.

Each of multiple grooved channels 210 on the sidewall surface of the head 150 can be a substantially J-shaped grooved channel to receive a post of a corresponding insertion tool as will be further described below. Note that the radial groove in fastener 120 may be located such that a respective sleeve 250 (as will be discussed in FIG. 6) may be rotated clock-wise or counter clock-wise to insert the post into the one or more grooved channels 210 and respective termination ends, as will be further discussed with regards to FIG. 6.

Figure 4:
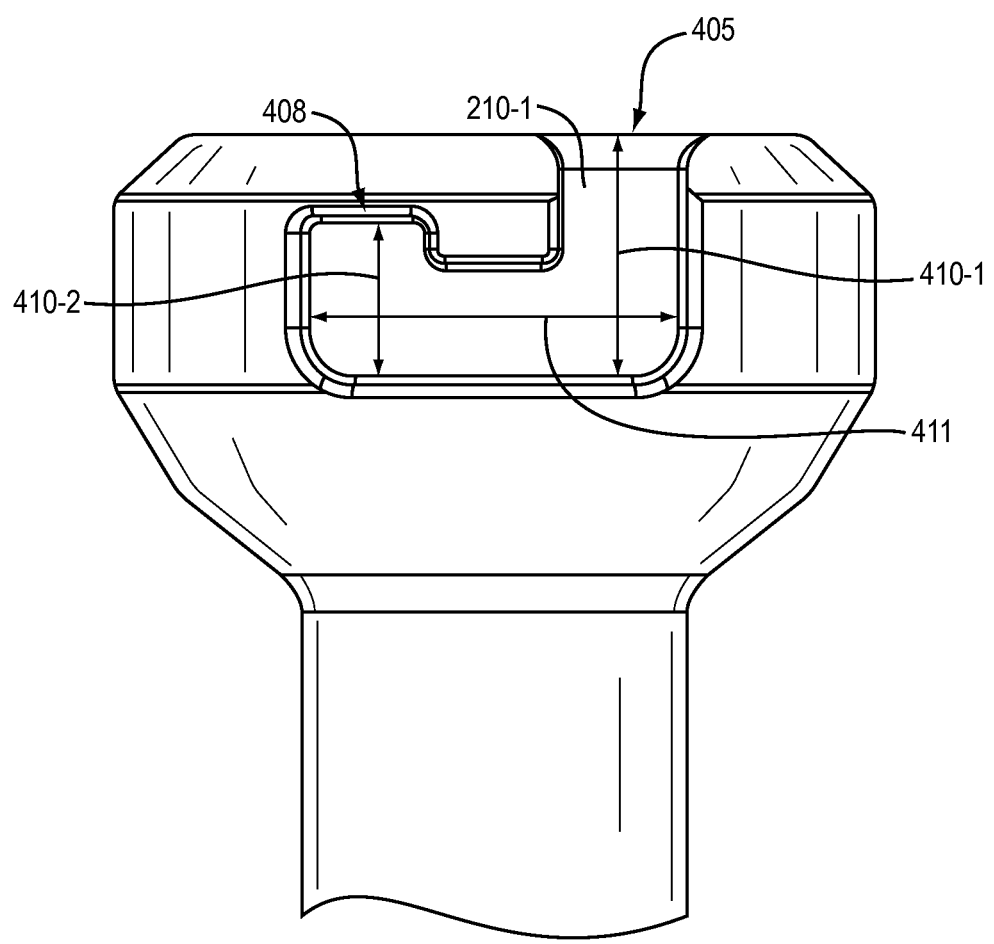
FIG. 4 is an example side view of a head of a fastener according to embodiments herein.

FIG. 4 is an example side view diagram of a head 150 of fastener 120 according to embodiments herein.

Each of the grooved channels 210 such as grooved channel 210-1 can include an opening end 405 and a termination end 408. Additionally, each of the grooved channels can include a first axial portion 410-1, a second axial portion 410-2, and a radial portion 411. The purposes of the opening end 405, the termination end 408, first axial portion 410-1, second axial portion 410-2, and radial portion 410-3 will be further described below.

Figure 5:
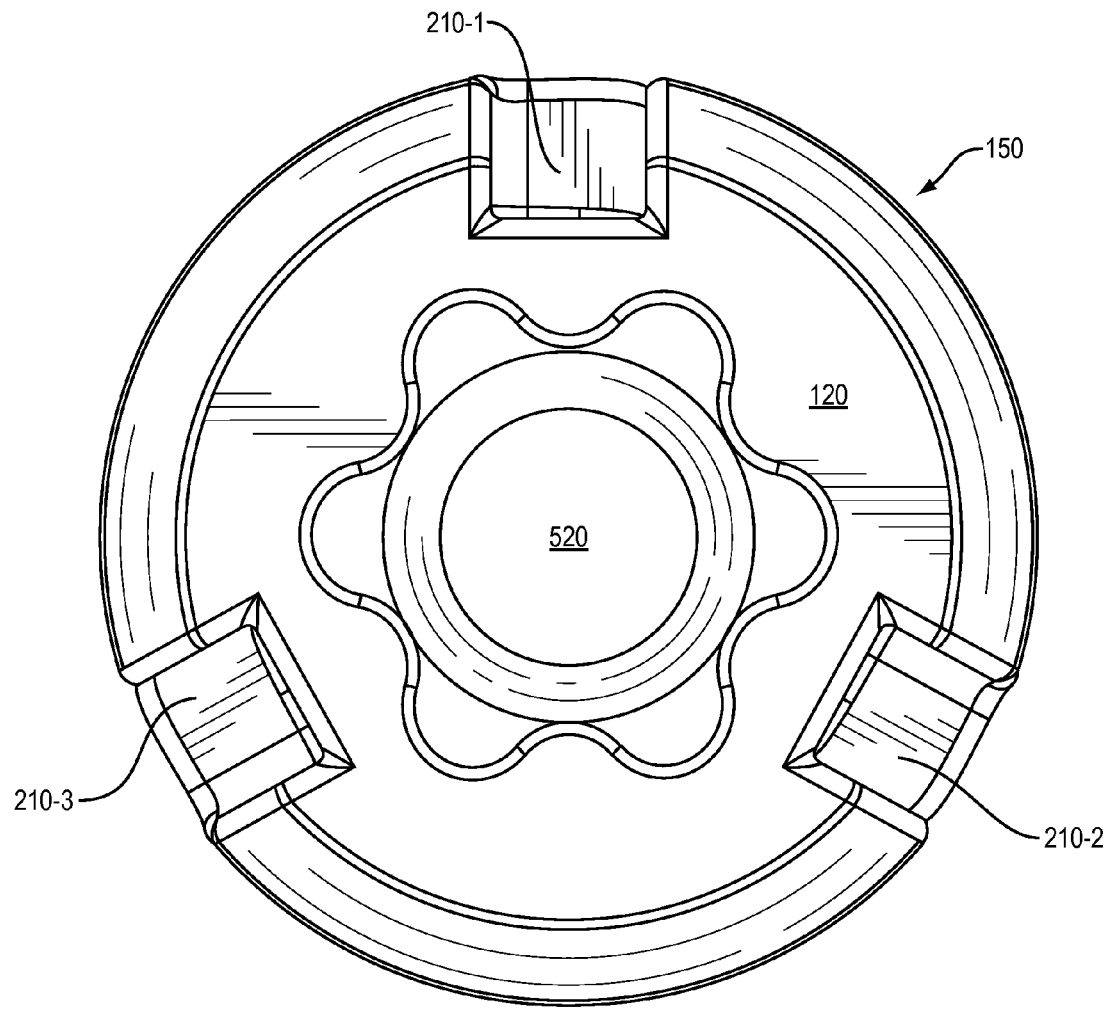
FIG. 5 is an example diagram illustrating a top view of a head of a fastener according to embodiments herein

FIG. 5 is an example diagram illustrating a top view of a head of a fastener according to embodiments herein.

As shown, a core 520 along an axial length of axis 198 of the fastener 120 can be hollowed for receiving a guide wire and/or allowing passage of matter. Such an embodiment is useful for applications in which the fastener 120 is a bone screw inserted into a bone. A large force is typically required to insert a screw into a bone. The guide wire can be inserted in the core 520 of fastener 120 to facilitate guidance of and insertion of the fastener 120 into a bone or other hard material.

As shown in this top view diagram of fastener 120 in FIG. 5, the grooved channels 210 on the fastener 120 can be circumferentially spaced apart from each other (e.g., 120 degrees apart for 3 grooved channels 210, 90 degrees apart for 4 grooved channels 210, etc.) on an outer surface or sidewall of the head 150 of the fastener 120.

As will be discussed further below, via occupation of a suitable protrusion into each of the grooved channels 210, a respective insertion tool (as discussed in the following figures) can apply a force on the head 150 of the fastener 120 to secure the fastener 120 to a driving tip of the insertion tool.

Figure 6:
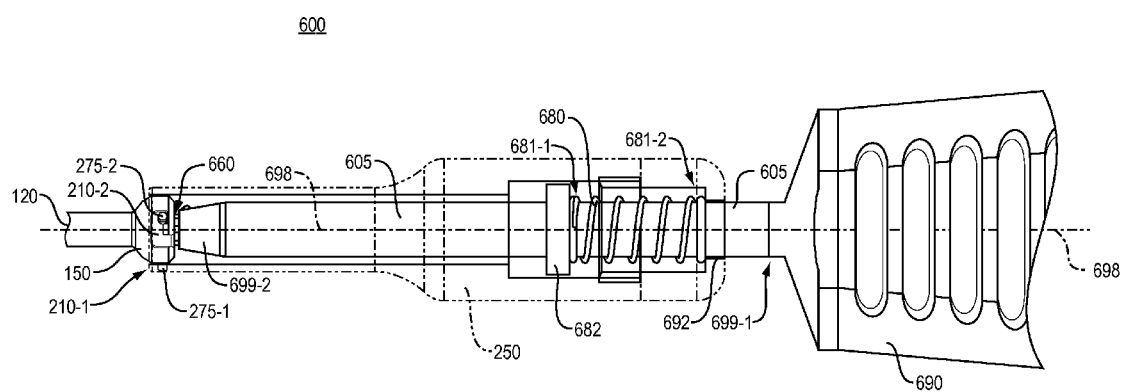
FIG. 6 is an example diagram illustrating an insertion tool and corresponding fastener according to embodiments herein.

FIG. 6 is an example diagram illustrating an insertion tool and corresponding fastener according to embodiments herein.

As shown, the insertion tool 600 includes a shaft 605, a handle 690 disposed at a first axial end 699-1 of axis 698 of the shaft 605, and a driving bit 660 disposed or fixedly attached at a second axial end 699-2 of axis 698 of the shaft 605. Accordingly, a user can control the driving bit 660 and respective shaft 605 via a force applied to the handle 690. The driving bit 660 of insertion tool 600 can be configured to occupy cavity 160 disposed in head 150 of fastener 120.

As shown, the insertion tool 600 can further include at least one post 275-1 (e.g., pin, finger, protrusion, etc.) to occupy at least one respective grooved channel 210-1 disposed on the head 150 of the fastener 120 to hold the fastener 120 onto the driving bit 660. The post 275-1 is movable via movement of the sleeve 250 along shaft 605. In one embodiment, the posts 275 are affixed to the sleeve 250.

Each of the posts 275 in sleeve 250 can be moved or inserted into a respective grooved channel 210 of the head 150 via sliding of the sleeve 250 along and/or rotating the sleeve 250 about the shaft 605. For example, the sleeve 250 can include multiple inward protruding posts 275 (e.g., post 275-1, post 275-2, post 275-3, . . . ) matching the pattern of respective grooved channels 210 on the head 150 of fastener 120. The posts 275 can be angularly spaced on the inside of the sleeve 250 to match a corresponding angular spacing of the grooved channels 210 with respect to each other. Accordingly, the posts 275 fixed to the inner surface of the sleeve 250 can fit into a keyway produced by the grooved channels 275 on the head 150 of the fastener 120.

The sleeve 250 of the insertion tool 600 can be spring-loaded (via spring 680) to pull the head 150 of the fastener 120 in a direction towards the handle 690 of the insertion tool 600. Note that the use of spring 680 is shown by way of non-limiting example only and that any type of suitable substitute such as a rubber block, etc., can be used in its place to exert a force of the sleeve 250.

More specifically, in one embodiment, the insertion tool 600 includes a stop 682 such as washer fixedly attached to the shaft 605 via a press fit, weld fit, pin fit, etc. A first end 681-1 of the spring 680 is in contact with the stop 682, which serves as first surface for compressing the spring 680. The spring 680 loosely fits around the shaft 605 so that the spring 680 compresses and decompresses based on movement of the sleeve 250 along the shaft 605. Sleeve 250 includes an inner, hollowed cavity in which the spring 680 and stop 682 reside. An inner diameter of the cavity in the sleeve 250 is reduced at sleeve end 692 nearer handle 690 such that the second end 681-2 of the spring 680 contacts the sleeve 250. Sleeve 250 slides along and rotates about shaft 605. Accordingly, when the user slides the sleeve along shaft 605 away from the handle 690, the spring 680 compresses further. At such time, the spring 680 applies a force on the sleeve end 692 (and thus sleeve 250) towards handle 690. Subsequent to engaging the posts 275 into respective grooved channel 210 of fastener 120, the user releases the sleeve 250. When released, the spring 680 applies a force on the sleeve and posts 275 towards the handle 698, holding the fastener 120 onto the driving bit 660.

As shown, an outer diameter of the sleeve 250 nearer the driving bit 660 of the shaft 605 can be smaller than an outer diameter of the sleeve 250 nearer the handle 690 end of the shaft 605. Accordingly, a user operating the insertion tool 600 can grasp the handle 690 with a first hand and easily grasp the sleeve 250 with the same or different hand to apply a force on the sleeve 250 to overcome an exertion force of the spring 680 by pushing the sleeve 250 away from the handle 690. In general, applying a force on the sleeve 250 away from handle 690 and aligning the posts 275 into the grooved channels 210 engages the posts 275 into the opening end 405 of the grooved channels 275 of the fastener 120.

As previously discussed, each of the grooved channels 210 such as grooved channel 210-1 on fastener 120 can include an opening end 405 and a termination end 408. The opening end 405 of the grooved channel 210-1 is configured to receive a respective post 275-1 on sleeve 250 of the insertion tool 600. For example, in accordance with one embodiment, the opening end 405 of grooved channel 210-1 can receive a post 275-1 moved in a direction toward the threads 135 on the fastener 120 as a result of sliding the sleeve 250 away from the handle 690 of the insertion tool 600. When the posts 275 of the sleeve 250 have been inserted far enough into the grooved channels 210 via movement of the sleeve along axis 698 away from the handle 690, the user rotates the sleeve 250 along radial portion 411 from first axial portion 410-1 to second axial portion 410-2 and subsequently releases the sleeve 250 to allow the post to slide along the second axial portion 410-2 toward the handle and lock the head 150 of the fastener 120 to the end of the sleeve 250. As previously discussed, releasing the sleeve 250 causes the sleeve 250 and respective posts 275 pull the head 150 of the fastener 120 onto the driving bit 660.

When in a locked position, the termination end 408 of grooved channel 210-1 prevents the posts 275 from sliding further in the head 150 when a force (such as a force produced by the spring 680) is applied to the sleeve 250 in a direction opposite the threads of the fastener 120. That is, the termination ends 408 of the grooved channels 210 prevent sliding of the posts 275 (and sleeve 250) in a direction away from the threads 135 of the fastener 120 when respective posts 275 of sleeve 250 come in contact with the termination ends 408 of grooved channels 275. In this manner, as discussed above, the posts 275 in sleeve 250 pull the head 150 of the fastener 120 onto the driving bit 660.

Figure 9:
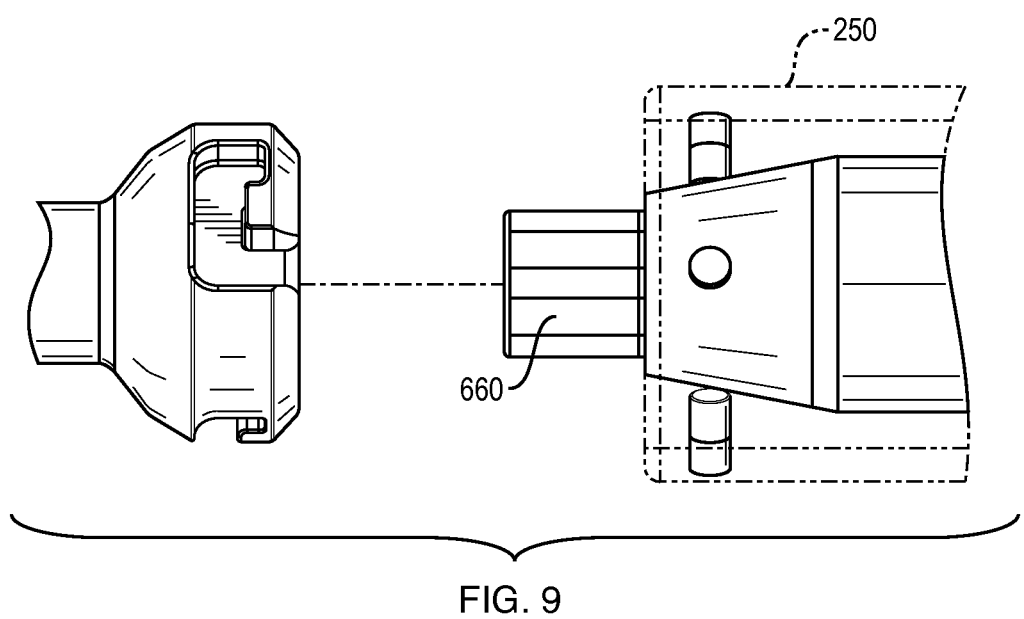
FIG. 9 is an example diagram illustrating an insertion tool when no force is applied to a respective sleeve according to embodiments herein.

In one embodiment, the termination end 408 of a respective grooved channel 210-1 in the fastener 120 prevents a radial movement of the sleeve 250 and/or post 275-1 about axis 198 of the fastener 120. In other words, when the post 275-1 is moved into and resides in the termination end 408 of the grooved channel 210-1, the post 275-1 in the termination end 408 can only be moved in an axial direction to the threads 135 of the fastener 120. Thus, the fastener 120 will not accidentally disengage from the head 150. To release the head 150 of the fastener 120 from the driving bit 660, the user applies a force to the sleeve 250 away from the handle 690, rotates the sleeve 250 along the radial portion 411, and releases the sleeve 250. A force of the spring 680 causes the sleeve 250 to slide to a rest position in the first axial portion 410-1, as shown in FIG. 9. The user then pulls the driving bit 660 out of the cavity 160 of fastener 120.

Figure 7:
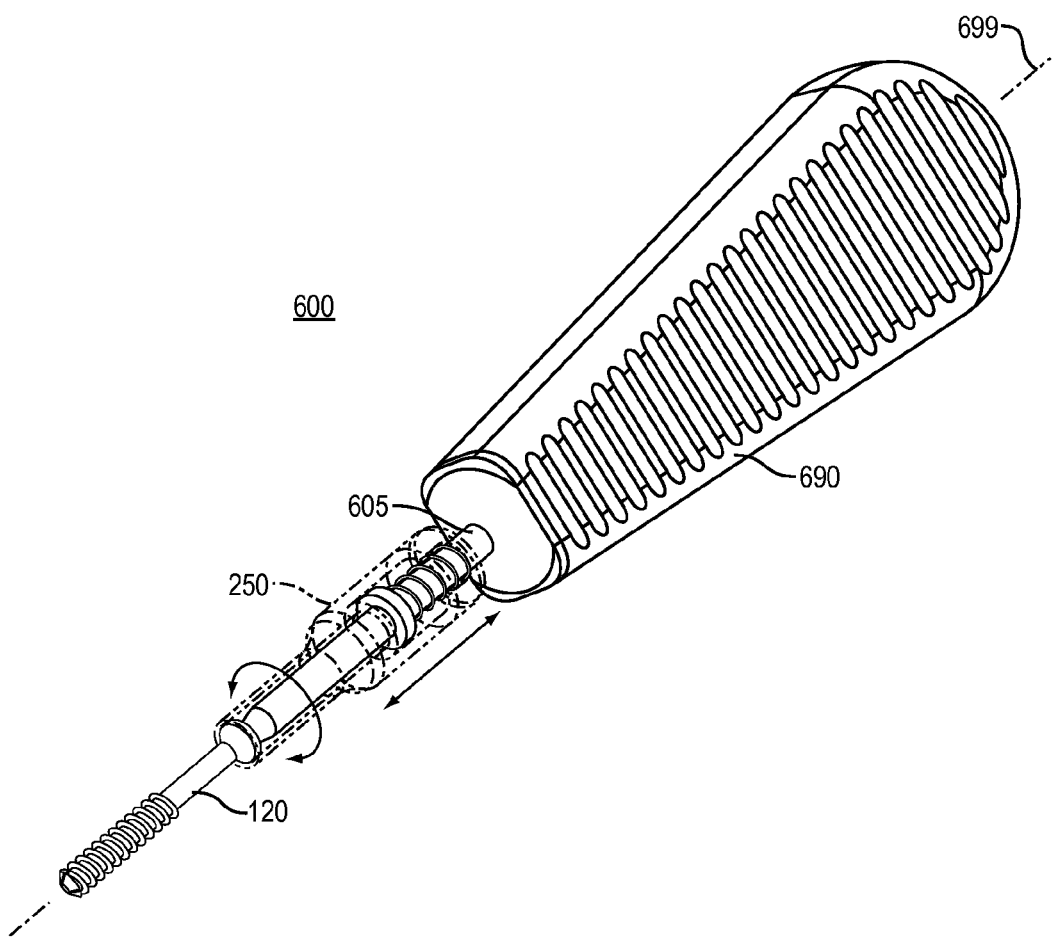
FIG. 7 is an example perspective view diagram of an insertion tool and corresponding fastener according to embodiments herein.

FIG. 7 is an example diagram illustrating a perspective view of the insertion tool and corresponding fastener according to embodiments herein.

As shown, in addition to sliding, the sleeve 250 of the insertion tool 600 can rotate around the shaft 605. As previously discussed, sliding and rotating the sleeve 250 facilitates engaging of the posts 275 into opening end 405 and locking into the respective termination ends 408 of the grooved channels 210. As will be further described below, sliding the sleeve 250 along an axis 698 parallel to the shaft 605 causes the posts 275 to slide through the respective opening ends 405 of grooved channels 210. The sleeve 250 can be slid along and rotated about the shaft 605 to facilitate movement of the posts 275 into the termination end 408 of the shaft and secure or lock the head 150 of the fastener 120 to the driving bit 660.

Figure 8:
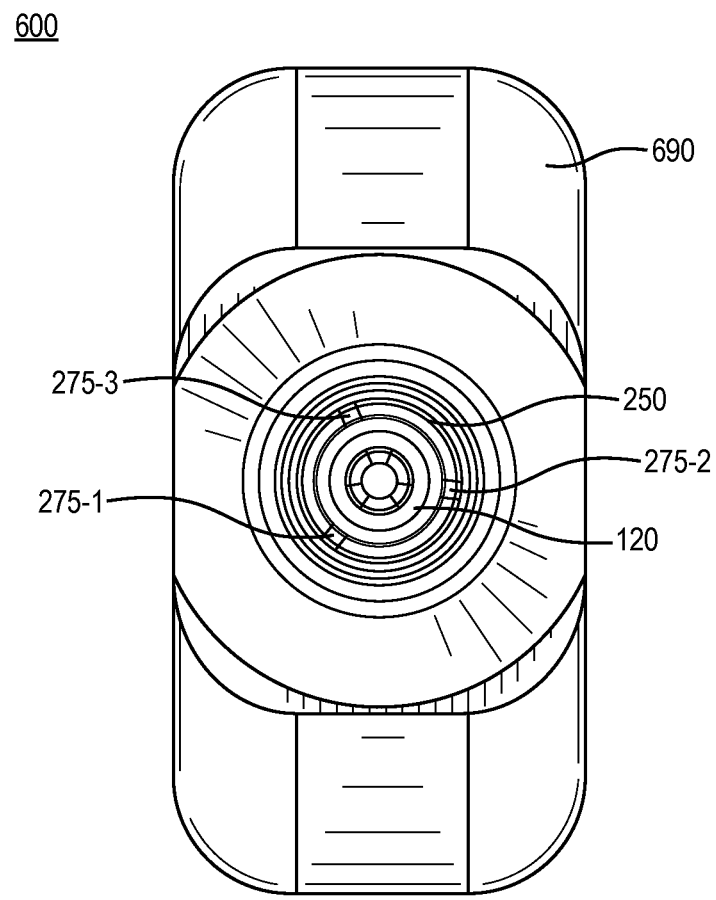
FIG. 8 is an example diagram illustrating a front view of an insertion tool and corresponding fastener according to embodiments herein.

FIG. 8 is an example diagram illustrating a front view of the fastener and the insertion tool 600 according to embodiments herein.

As shown, the shaft of the insertion tool 600 can be hollow. As previously discussed, the fastener 120 coupled to the driving bit 660 also can be hollow. Accordingly, the previously discussed guide-wire can be pulled through a combination of the shaft 660 of the insertion tool 600 and the fastener 120 to facilitate guidance and insertion of the fastener 120 into an object such as a bone during surgery.

FIG. 9 is an example diagram illustrating further aspects of an insertion tool according to embodiments herein.

Figure 10:
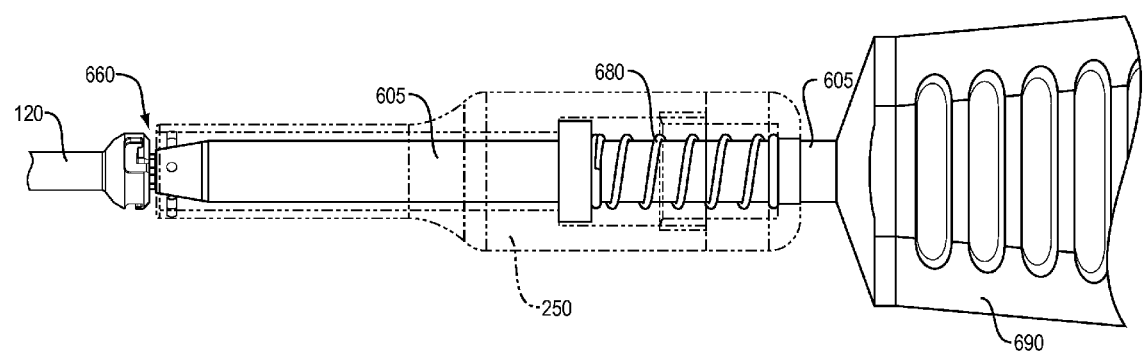
FIG. 10 is an example diagram illustrating insertion of a driving bit into a cavity of a fastener according to embodiments herein.

As shown, when no force is applied to the spring-loaded sleeve 250, the sleeve 250 of the insertion tool 600 can reside in a resting position in which the driving tip 660 of the insertion tool 600 is exposed for access. In one embodiment, the spring 680 pushes sleeve 250 towards handle 690 so that the driving bit 660 is exposed as shown in FIG. 9. In such a position, the user can insert the driving tip 660 of the insertion tool into a cavity 160 of the fastener 120 as shown in FIG. 10. Accordingly, an assembly, to which the posts 275 are affixed, such as a sleeve 250, can be configured to slide along the shaft 605 to slide sleeve 250 over driving bit 660 as previously discussed. Based on sliding and rotating of the sleeve with respect to shaft 605, as previously disclosed, the user engages the posts 275 into grooved channels 210 as shown in FIG. 11.

Figure 11:
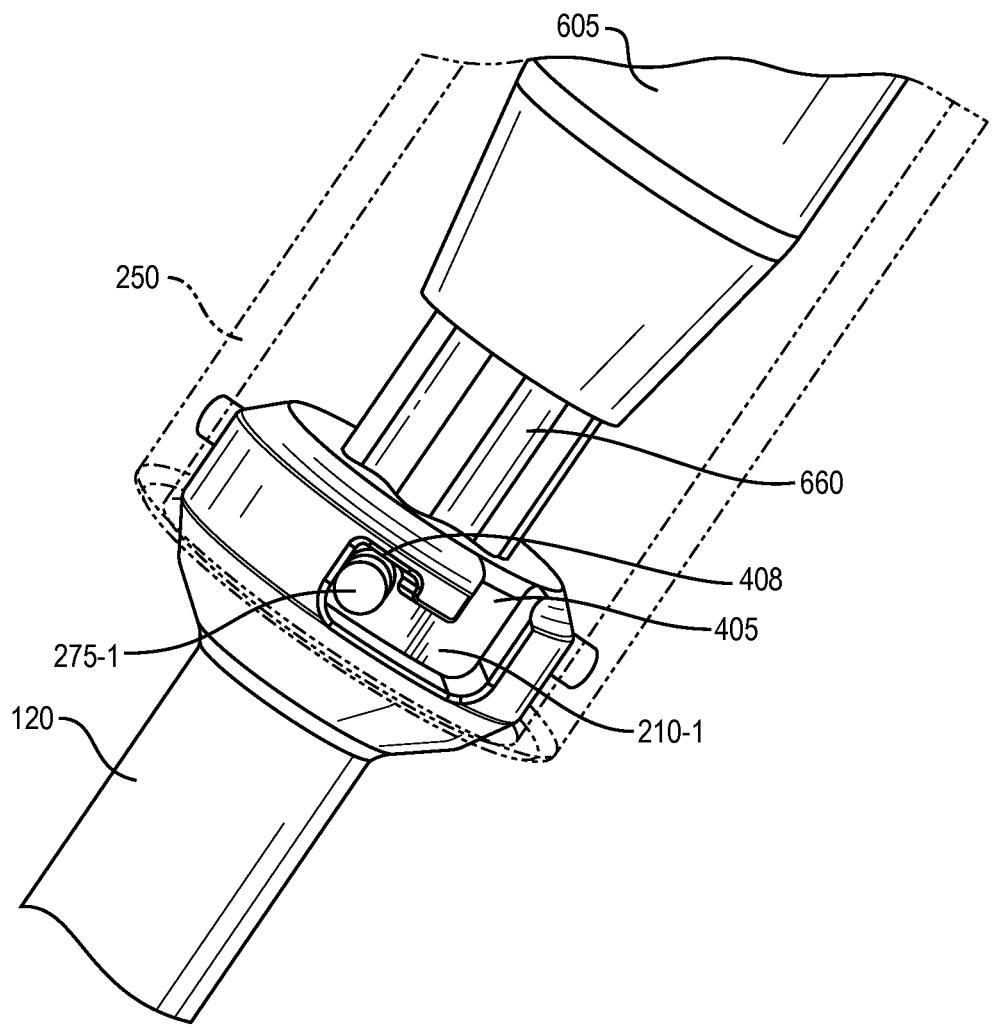
FIG. 11 is an example diagram illustrating engagement of posts into grooved channels of a fastener according to embodiments herein.

FIG. 11 is an example diagram illustrating a perspective view of a fastener engaged in an insertion tool according to embodiments herein.

As shown, sleeve 250 includes post 275-1 engaged in grooved channel 210-1. As previously discussed, spring 680 pulls sleeve 250 and corresponding post 275-1 into termination end 408 of grooved channel 210-1 towards handle 690. In a similar manner, each of one or more posts 275 of sleeve 250 secures the head 150 of fastener 120 to the driving bit 660.

Note that embodiments herein can include swapping the posts 275 and grooved channels 210. For example, as discussed below, the sleeve 250 of insertion tool 600 can be configured to include channels instead of posts 275; the fastener can be configured to include posts instead of grooved channels 210.

Figure 12:
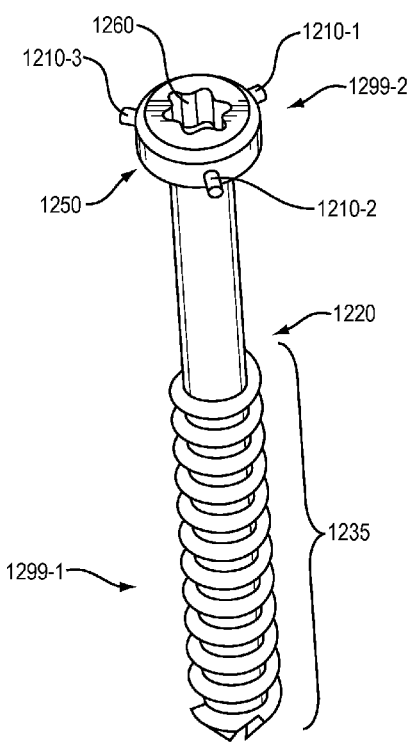
FIG. 12 is an example perspective view illustrating a fastener including posts according to embodiments herein.

FIG. 12 is an example perspective view illustrating a fastener including posts according to embodiments herein.

In accordance with one embodiment herein, fastener 1220 includes threads 1235 and a head 1250. The threads 1235 are disposed at a first axial end 1299-1 of the fastener 1220. The head 1250 is disposed at a second axial end 1299-2 of the fastener 1220. The head 1250 of the fastener 1220 includes a cavity 1260 in which to receive a driving bit 660 disposed at an end of an insertion tool 600 such as a screwdriver. The head 1250 of the fastener 1220 includes posts 1210 (e.g., post 1210-1, post 1210-2, post 1210-3) protruding axially outward from the head 1250.

By way of a non-limiting example, the cavity 1260 in fastener 1220 is configured to receive a torx bit disposed at the end of an insertion tool. However, note that the cavity 1260 of head 1250 can be bored to receive any suitable type of driving bit (e.g., a phillips head bit, flat head bit, hex bit, socket, etc.).

Figure 13:
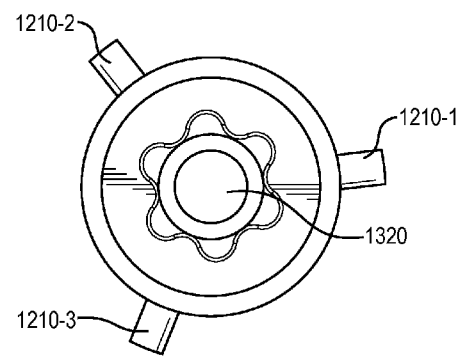
FIG. 13 is an example top view illustrating a fastener including posts according to embodiments herein.

FIG. 13 is an example top view illustrating a fastener including posts according to embodiments herein.

As shown, a core 1320 through a length of fastener 1220 is hollow for receiving a guide wire and/or allowing passage of matter. Such an embodiment is useful for applications in which the fastener 1220 is a bone screw inserted into a bone. A large force may be required to insert a screw into a bone. The guide wire can be inserted in the core 1320 of fastener 1220 to facilitate guidance of and insertion of the fastener 1220 into a bone or other hard material.

As shown in this top view diagram of fastener 1220, the posts 1210 on the fastener 1220 can be circumferentially spaced apart from each other (e.g., 120 degrees apart for 3 posts 1210, 90 degrees apart for 4 posts 1210, etc.) on an outer surface or sidewall of the head 1250 of the fastener 1220.

Figure 14:
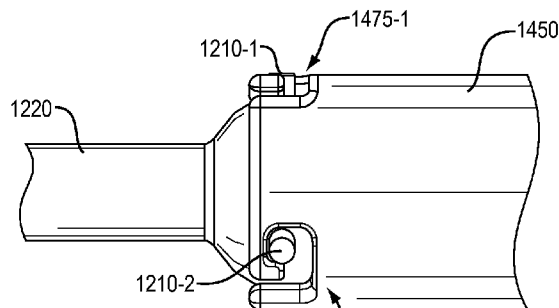
FIG. 14 is an example diagram illustrating engagement of posts into respective grooved channels of an insertion tool according to embodiments herein.

FIG. 14 is an example diagram illustrating replacement of the posts 275 in the sleeve 250 of the insertion tool 600 with respective channels 1475 (e.g., 1475-1, channel 1475-2, etc.) according to embodiments herein.

In the embodiment of FIG. 14, the insertion tool 600 operates in the same way as discussed above even though the sleeve 250 is replaced with sleeve 1450 as shown in FIG. 14. To secure the fastener 1220 to driving bit 660, the user slides and rotates sleeve 1450 to engage posts 1475 into respective channels 1475. As previously discussed, the sleeve 1450 can be spring-loaded to pull the head of the fastener 1220 onto the respective driving bit 660 of insertion tool 600. In this embodiment, however, the channels 1475 of sleeve 1450 apply a force to posts 1210 of fastener 1220 to secure the fastener 1220 to the driving bit 660.

Figure 15:
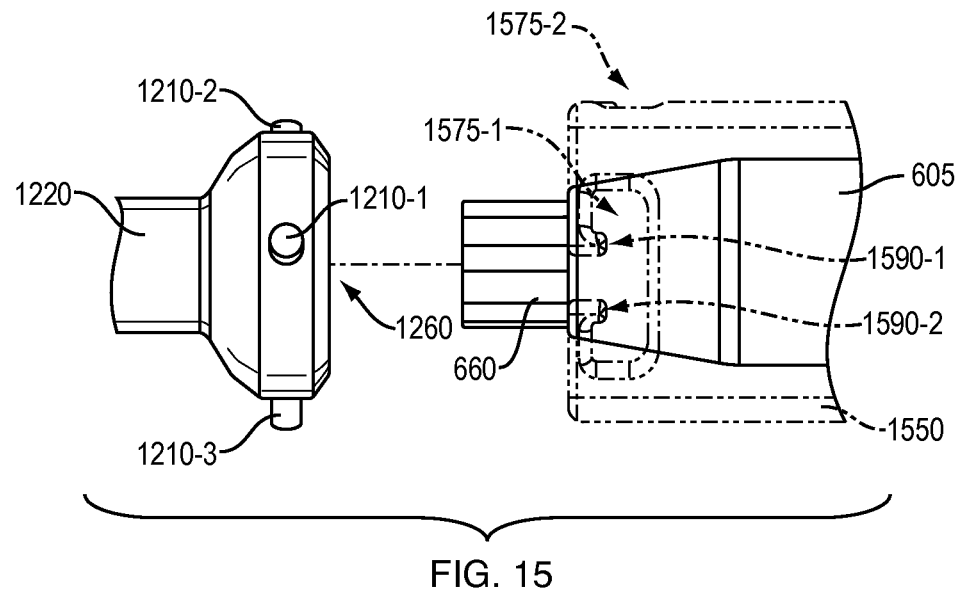
FIG. 15 is an example diagram illustrating a T-shaped grooved channel in a sleeve of an insertion tool according to embodiments herein.

FIG. 15 is an example diagram illustrating a T-shaped grooved channel in a sleeve of an insertion tool according to embodiments herein. As shown, example sleeve 1550 of insertion tool 600 includes channels 1575 (e.g., channel 1575-1, channel 1575-2, . . . ) for receiving respective posts 1210 disposed on fastener 1220. Each respective channel 1575 can include an opening 1610 and detents 1590 (e.g., detent 1590-1, detent 1590-2) to prevent the sleeve 1550 from rotating subsequent to engaging of the respective posts 1210 into channels 1575.

Figure 16:
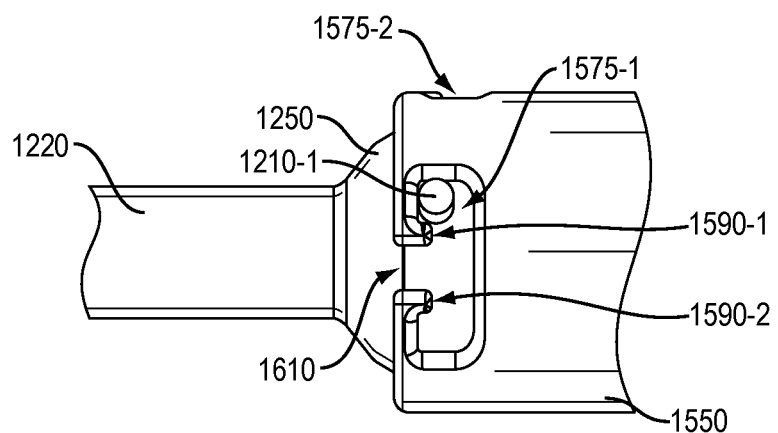
FIG. 16 is an example diagram illustrating engagement of posts on a fastener into respective grooved channels of a sleeve of an insertion tool according to embodiments herein.

FIG. 16 is an example diagram illustrating engagement of posts on a fastener into respective grooved channels of a sleeve of an insertion tool according to embodiments herein. Once the posts are received through opening 1610, the sleeve 1550 is rotated either clockwise or counter-clockwise and then released. As shown, sleeve 1550 can be spring-loaded such that release of the sleeve 1550 as shown in FIG. 16 results in pulling of the head 1250 of fastener 1220 onto driving bit 660. While in the released position, a respective detent 1590 of the channel 1575-1 prevents rotation of the sleeve 1550 so that posts 1210 do not accidentally disengage from the channels 1575 during insertion of the fastener 1220 into work material. The fastener 1220 can be released after insertion via application of a force on the sleeve towards the head 1250, rotating of the sleeve 1550, and releasing of the sleeve 1550 such that post 1210-1 releases from channel 1575-1 at respective opening 1610.

Figure 17:
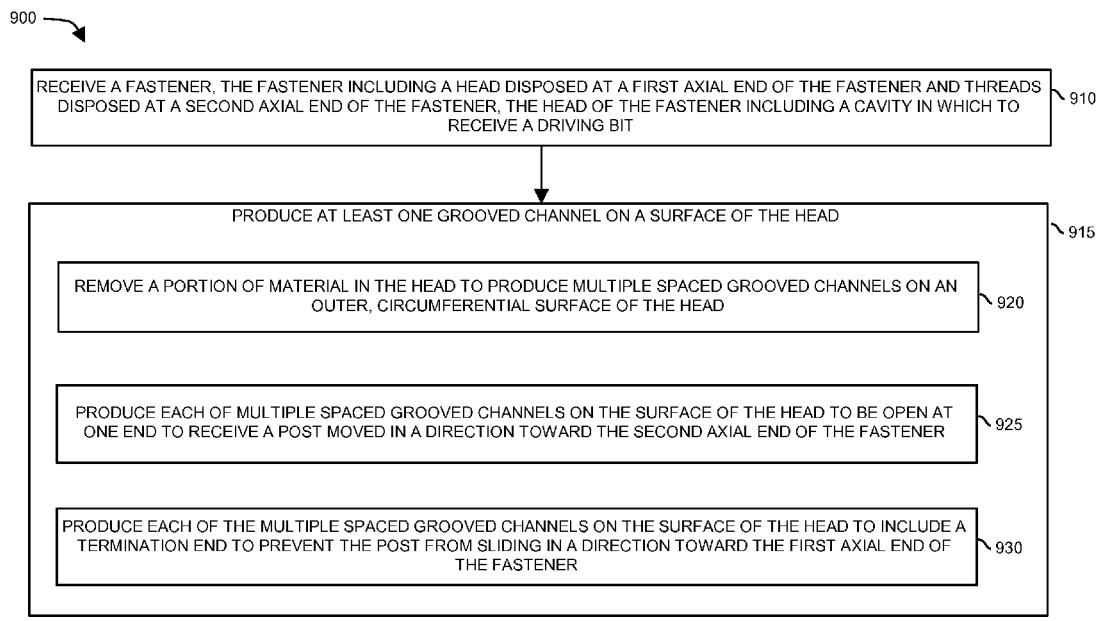
FIG. 17 is a flowchart illustrating an example method of manufacturing a fastener according to embodiments herein.

FIG. 17 is a flowchart 900 illustrating a method of manufacturing a fastener according to embodiments herein.

In step 910, a machine receives a fastener 120. The fastener 120 includes a head 150 disposed at axial end 199-2 of the fastener 120 and threads 135 disposed at axial end 199-1 of the fastener 120. The head 150 of the fastener 120 includes a cavity 160 in which to receive a driving bit 660.

In step 915, the machine removes a portion of material in the head 150 to produce at least one grooved channel 275 (e.g., cavity) on a surface of the head 150.

In sub-step 920, the machine removes a portion of material in the head 150 to produce multiple spaced grooved channels 275 on an outer, circumferential surface of the head 150.

In sub-step 925, the machine produces each of multiple spaced grooved channels 275 on the surface of the head 150 to be open at one end (e.g., the open end 405) to receive a post 275 moved in a direction toward the axial end 199-1 of the fastener 120.

In sub-step 930, the machine produces each of the multiple spaced grooved channels 275 on the surface of the head 150 to include a termination end 408 to prevent the post 275 from sliding in a direction toward the axial end 199-2 of the fastener 120.

Figure 18:
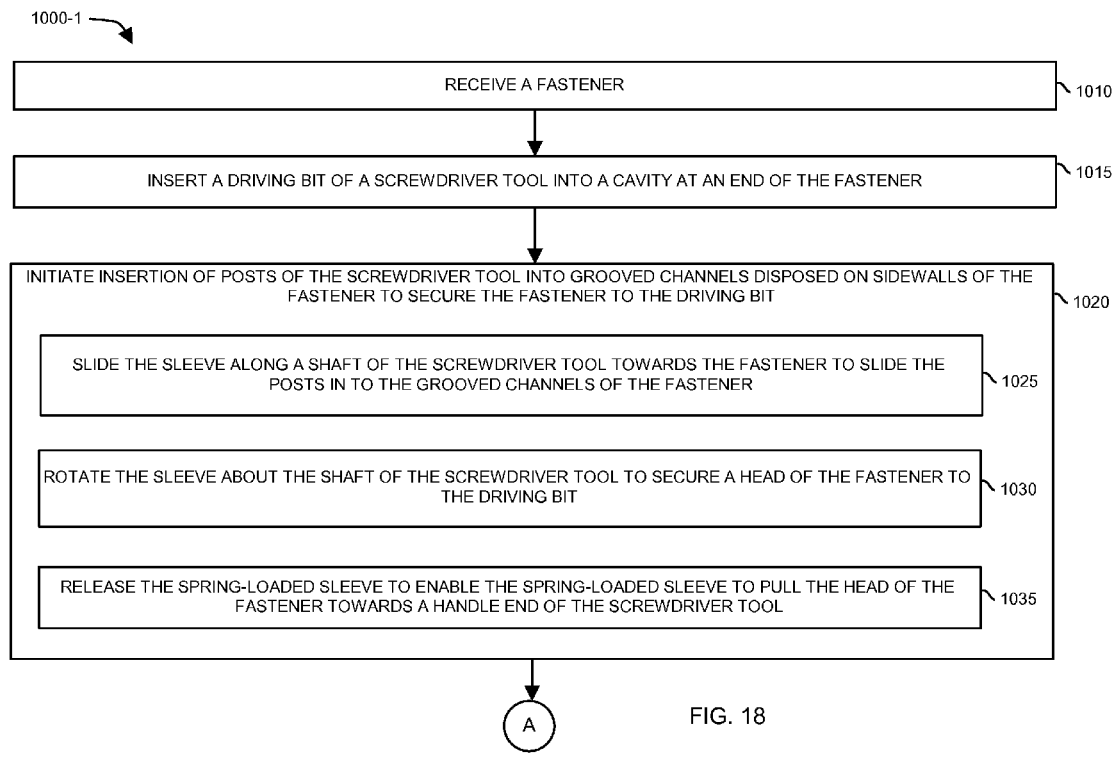
FIGS. 18 and 19 combine to form a flowchart illustrating example steps of a user utilizing a first version of the insertion tool and corresponding fastener according to embodiments herein.
Figure 19:
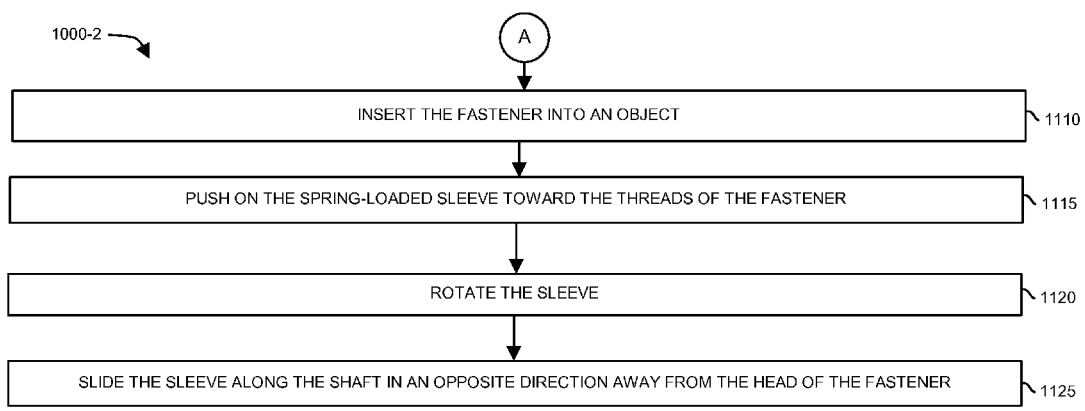

FIGS. 18 and 19 combine to form a flowchart 1000 (e.g., flowchart 1000-1 and flowchart 1000-2) illustrating a method of utilizing an insertion tool and fastener according to embodiments herein.

In step 1010, a user receives a fastener 120.

In step 1015, the user inserts a driving bit 660 of a screwdriver tool (e.g., insertion tool 600) into a cavity 160 at an end of the fastener 120.

In step 1020, the user initiates insertion of posts 275 of the screwdriver tool into grooved channels 210 disposed on sidewalls of the fastener 120 to secure the fastener 120 to the driving bit 660.

In sub-step 1025, the user slides the sleeve 250 along a shaft 605 of the screwdriver tool towards the fastener 120 to slide the posts 275 axially into the grooved channels 210 of the fastener 120.

In sub-step 1030, the user rotates the sleeve 250 about the shaft 605 of the screwdriver tool to secure a head 150 of the fastener 120 to the driving bit 660.

In sub-step 1035, the user releases the spring-loaded sleeve 250 to enable the spring-loaded sleeve 250 to pull the head 150 of the fastener 120 towards a handle end of the screwdriver tool.

In step 1110, the user inserts the fastener 120 into an object.

In step 1115, the user pushes on the spring-loaded sleeve 250 towards the threads of the fastener 120.

In step 1120, the user rotates the sleeve 250.

In step 1125, the user slides the sleeve 250 along the shaft in an opposite direction away from the head 150 of the fastener 120. This step can include releasing the sleeve 250 so that the spring 680 causes the sleeve 250 to slide axially along shaft 605 towards the handle 690, disengaging the posts 275 from the respective grooved channels 210.

Figure 20:
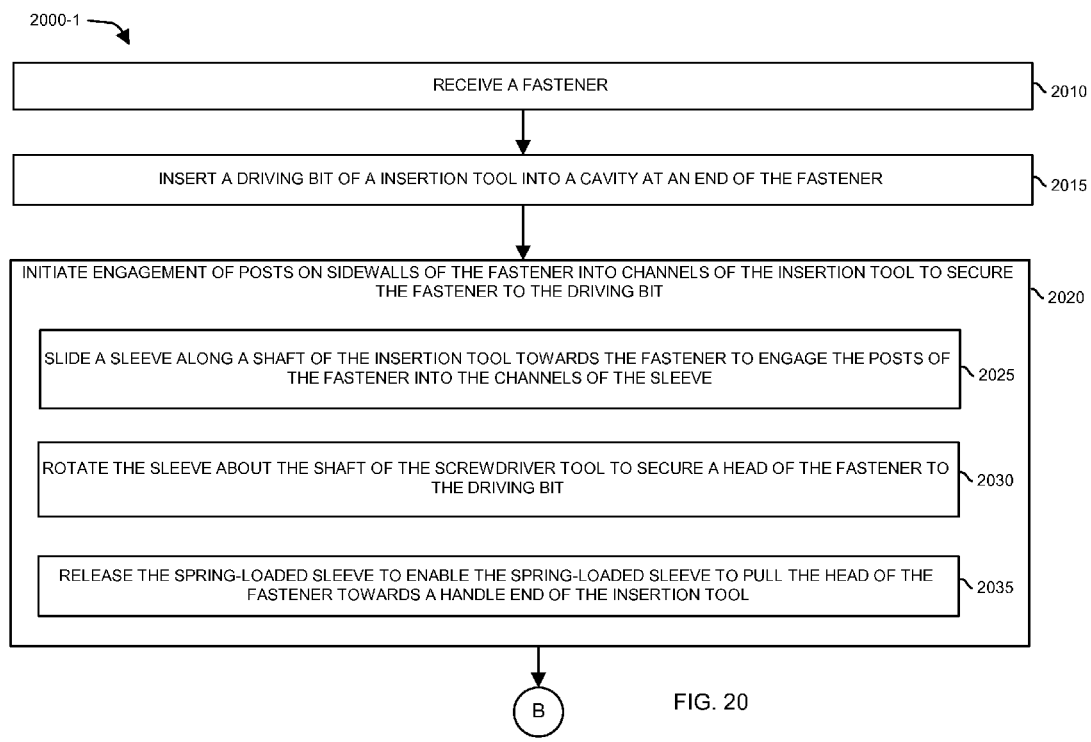
FIGS. 20 and 21 combine to form a flowchart illustrating example steps of a user utilizing a second version of the insertion tool and corresponding fastener according to embodiments herein.
Figure 21:
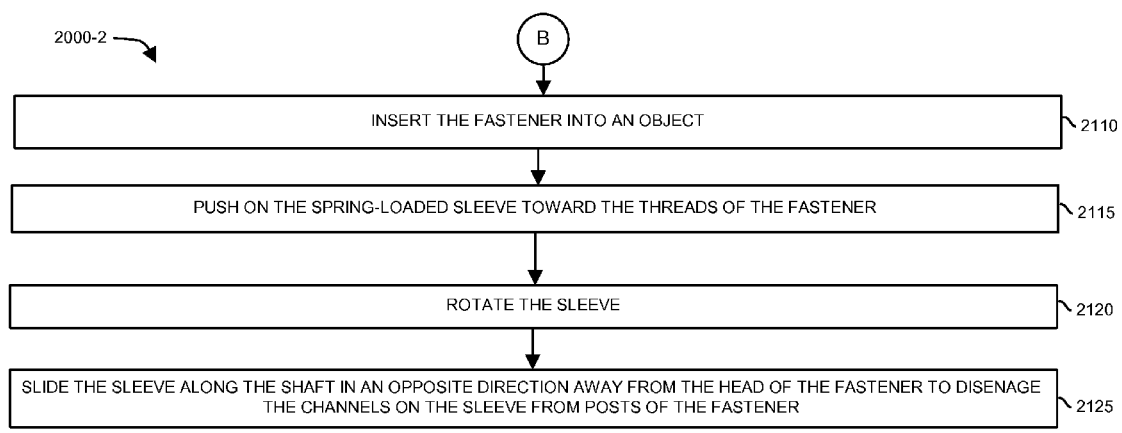

FIGS. 20 and 21 combine to form a flowchart 2000 (e.g., flowchart 2000-1 and flowchart 2000-2) illustrating a method of utilizing an insertion tool 600 and fastener 1220 according to embodiments herein.

In step 2010, a user receives a fastener 1220.

In step 2015, a user inserts a driving bit 660 of the insertion tool 600 into a cavity 1260 at an end of the fastener 1220.

In step 2020, a user initiates engagement of posts 1210 on sidewalls of the fastener 1220 into channels 1475 of the insertion tool 600 to secure the fastener 1220 to the driving bit 660.

In step 2025, a user slides sleeve 1450 along a shaft 605 of the insertion tool 600 towards the fastener 1220 to engage the posts 1210 of the fastener 1220 into the channels 1475 of the sleeve 1450.

In step 2030, a user rotates the sleeve 1450 about the shaft 605 of the insertion tool 600 to secure a head 1250 of the fastener 1220 to the driving bit 660.

In step 2035, a user releases the spring-loaded sleeve 1450 to enable the spring-loaded sleeve 1450 to pull the head 1250 of the fastener 1220 towards a handle end of the insertion tool 600.

In step 2110 of FIG. 21, the user inserts the fastener 1220 into an object such as a bone.

In step 2115, subsequent to inserting the fastener 1220 into the object, the user pushes on the spring-loaded sleeve 1450 towards the threads of the fastener 1220.

In step 2120, the user rotates the sleeve 1450.

In step 2125, the user slides the sleeve 1450 along the shaft 605 in an opposite direction away from the head 1250 of the fastener 1220. This step can include releasing the sleeve 1450 so that the spring 680 in the insertion tool 600 causes the sleeve 1450 to slide axially along shaft 605 towards the handle 690, disengaging the channels 1475 from the respective posts 1210 on the fastener 1220.

Note again that techniques herein are well suited for use in fastener and screwdriver applications. However, it should be noted that embodiments herein are not limited to use in such applications and that the techniques discussed herein are well suited for other applications as well.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

What is claimed is:

1. An insertion tool comprising:
a shaft;
a handle disposed at a first axial end of the shaft;
a driving bit disposed at a second axial end of the shaft;
at least one post, coupled to a sleeve that slides along the shaft, to occupy at least one respective grooved channels disposed on a head of a fastener to hold the fastener to the driving bit; and
wherein the sleeve is movable rotationally and axially around the shaft to facilitate engaging the at least one post into the at least one respective grooved channels.

2. The insertion tool as in claim 1, wherein the at least one post is movable both axially and radially to insert the at least one post into the at least one respective grooved channels.

3. The insertion tool as in claim 1, wherein the sleeve is spring-loaded.

4. The insertion tool as in claim 1, wherein a diameter of the sleeve nearer the first axial end of the shaft is greater than a diameter of the sleeve nearer the second axial end of the shaft.

5. The insertion tool as in claim 1, wherein the at least one post is configured to slide along an axis parallel to the shaft and rotate about the shaft to lock the head of the fastener to the driving bit.

6. The insertion tool as in claim 1, wherein the driving bit is fixedly attached to the shaft and the shaft is fixedly attached to the handle.

7. An insertion tool comprising:
a shaft;
a handle disposed at a first axial end of the shaft;
a driving bit disposed at a second axial end of the shaft;
at least one post, affixed to a sleeve that slides along the shaft, to occupy at least one respective grooved channels disposed on a head of a fastener to hold the fastener to the driving bit; and
wherein the sleeve is spring-loaded.

8. An insertion tool comprising:
a shaft;
a handle disposed at a first axial end of the shaft;
a driving bit disposed at a second axial end of the shaft; and
at least one post, movable with respect to the shaft, to occupy at least one respective grooved channels disposed on a head of a fastener to hold the fastener to the driving bit; and
wherein the shaft is hollow.

9. The insertion tool as in claim 8, wherein a sleeve, on which the at least post is affixed, is movable rotationally and axially around the shaft to facilitate engaging the at least one post into the at least one respective grooved channels.

10. A method comprising:
receiving a fastener;
inserting a driving bit of a screwdriver tool into a cavity at an end of the fastener; and
initiating insertion of posts of the screwdriver tool into grooved channels disposed on sidewalls of the fastener to secure the fastener to the driving bit.

11. The method as in claim 10, wherein initiating insertion of the posts includes:

sliding a sleeve along a shaft of the screwdriver tool to insert the posts in to the grooved channels.

12. The method as in claim 10, wherein the posts are fixed to a sleeve of the screwdriver tool; and wherein initiating insertion of the posts includes sliding the sleeve along a shaft of the screwdriver tool towards the fastener to slide the posts in to the grooved channels.

13. The method as in claim 12, wherein initiating insertion of the posts further includes:

rotating the sleeve about the shaft of the screwdriver tool to secure a head of the fastener to the driving bit.

14. The method as in claim 13, wherein the sleeve is a spring-loaded sleeve, the method further comprising:

releasing the spring-loaded sleeve to enable the spring-loaded sleeve to pull the head of the fastener towards a handle end of the screwdriver tool.

15. A fastener comprising:

threads, the threads disposed on a first axial end of the fastener;

a head, the head disposed on a second axial end of the fastener; and the head comprising:

a cavity, at least one post; and wherein the at least one post is disposed on an outer sidewall surface of the head.

16. The fastener as in claim 15, wherein the at least one post includes multiple posts.

17. The fastener as in claim 16, wherein a core along an axial length of the fastener is hollow.

18. The fastener as in claim 16, wherein the at least one post includes at least three posts, each of the at least three posts circumferentially spaced apart from each other on the outer sidewall surface of the head.

19. The fastener as in claim 15, wherein a core along an axial length of the fastener is hollow.

20. The fastener as in claim 15, wherein the at least one post includes at least three posts, each of the at least three posts circumferentially spaced apart from each other on the outer sidewall surface of the head.

21. A fastener comprising:

threads, the threads disposed on a first axial end of the fastener;

a head, the head disposed on a second axial end of the fastener; and the head comprising:

a cavity, at least one post; and wherein a core along an axial length of the fastener is hollow.

22. The fastener as in claim 21, wherein the at least one post includes at least three posts, each of the at least three posts circumferentially spaced apart from each other on the outer sidewall of the head.

23. A fastener comprising:

threads, the threads disposed on a first axial end of the fastener;

a head, the head disposed on a second axial end of the fastener; and the head comprising:

a cavity, at least one post; and wherein the at least one post includes at least three posts, each of the at least three posts circumferentially spaced apart from each other on an outer sidewall of the head.

24. An insertion tool comprising:

a shaft;

a handle disposed at a first axial end of the shaft;

a driving bit disposed at a second axial end of the shaft;

at least one channel to receive at least one respective post disposed on a head of a fastener to hold the fastener to the drive bit; and wherein the at least one channel is movable both axially and radially to receive the at least one respective post disposed on the head of the fastener.

25. The insertion tool as in claim 24, wherein the shaft is hollow.

26. The insertion tool as in claim 24, wherein the at least one channel resides on a sleeve that slides along the shaft; and wherein the at least one channel on the sleeve is substantially T-shaped to receive the at least one respective post disposed on the head of the fastener.

27. An insertion tool comprising:

a shaft;

a handle disposed at a first axial end of the shaft;

a driving bit disposed at a second axial end of the shaft;

at least one channel to receive at least one respective post disposed on a head of a fastener to hold the fastener to the drive bit; and wherein the at least one channel resides in a sleeve that slides along the shaft.

28. The insertion tool as in claim 27, wherein the sleeve is spring-loaded.

29. The insertion tool as in claim 27, wherein the sleeve is movable rotationally and axially around the shaft to facilitate engaging the at least one channel into the at least one respective posts of the fastener.

30. The insertion tool as in claim 27, wherein the driving bit is fixedly attached to the shaft and the shaft is fixedly attached to the handle.

31. The insertion tool as in claim 27, wherein the at least one channel is movable both axially and radially to receive the at least one respective post disposed on the head of the fastener.

32. The insertion tool as in claim 27, wherein the at least one channel is configured to slide along an axis parallel to the shaft and rotate about the shaft to lock the head of the fastener to the driving bit.

33. The insertion tool as in claim 27, wherein the shaft is hollow.

34. The insertion tool as in claim 27, wherein the at least one channel resides on the sleeve, and the sleeve slides along the shaft; and wherein the at least one channel on the sleeve is substantially T-shaped to receive the at least one respective post disposed on the head of the fastener.

35. An insertion tool comprising:

a shaft;

a handle disposed at a first axial end of the shaft;

a driving bit disposed at a second axial end of the shaft;

at least one channel to receive at least one respective post disposed on a head of a fastener to hold the fastener to the drive bit; and wherein the at least one channel is configured to slide along an axis parallel to the shaft and rotate about the shaft to lock the head of the fastener to the driving bit.

36. The insertion tool as in claim 35, wherein the at least one channel is movable both axially and radially to receive the at least one respective post disposed on the head of the fastener.

37. The insertion tool as in claim 35, wherein the shaft is hollow.

38. The insertion tool as in claim 35, wherein the at least one channel resides on a sleeve that slides along the shaft; and
wherein the at least one channel on the sleeve is substantially T-shaped to receive the at least one respective post disposed on the head of the fastener.

39. An insertion tool comprising:
a shaft;
a handle disposed at a first axial end of the shaft;
a driving bit disposed at a second axial end of the shaft;
at least one channel to receive at least one respective post disposed on a head of a fastener to hold the fastener to the drive bit; and
wherein the shaft is hollow.

40. The insertion tool as in claim 39, wherein the at least one channel is movable both axially and radially to receive the at least one respective post disposed on the head of the fastener.

41. The insertion tool as in claim 39, wherein the at least one channel resides on a sleeve that slides along the shaft; and
wherein the at least one channel on the sleeve is substantially T-shaped to receive the at least one respective post disposed on the head of the fastener.

42. A method comprising:
receiving a fastener, the fastener including a head disposed at a first axial end of the fastener and threads disposed at a second axial end of the fastener, the head of the fastener including a cavity in which to receive a driving bit; and
producing a post on the head; and
wherein producing the post further comprises producing multiple spaced posts on an outer, circumferential surface of the head.

43. A method comprising:
receiving a fastener;
inserting a driving bit of a screwdriver tool into a cavity at an end of the fastener; and
initiating engagement of posts on sidewalls of the fastener into channels of the screwdriver tool to secure the fastener to the driving bit.

44. The method as in claim 43, wherein initiating engagement of the posts includes:
sliding a sleeve along a shaft of the screwdriver tool to engage the posts of the fastener into the channels.

45. The method as in claim 43, wherein the channels are disposed in a sleeve of the screwdriver tool; and
wherein initiating engagement of the posts includes sliding the sleeve along a shaft of the screwdriver tool towards the fastener to engage the posts into the channels.

46. The method as in claim 45, wherein initiating engagement of the posts further includes:
rotating the sleeve about the shaft of the screwdriver tool to secure a head of the fastener to the driving bit.

47. The method as in claim 46, wherein the sleeve is a spring-loaded sleeve, the method further comprising:
releasing the spring-loaded sleeve to enable the spring-loaded sleeve to pull the head of the fastener towards a handle end of the screwdriver tool.

48. An insertion tool comprising:
a shaft;
a handle disposed at a first axial end of the shaft;
a driving bit disposed at a second axial end of the shaft;
at least one channel to receive at least one respective post disposed on a head of a fastener to hold the fastener to the drive bit; and
wherein the at least one channel resides on a sleeve that slides along the shaft; and
wherein the at least one channel on the sleeve is substantially T-shaped to receive the at least one respective post disposed on the head of the fastener.

* * * * *